United States Patent [19]

Ellis Margaret D. et al.

[11] Patent Number: 4,537,991

[45] Date of Patent: Aug. 27, 1985

[54] PROCESS FOR THE DIRECT ACETYLATION OF AROMATIC AMINES

[75] Inventors: Ellis Margaret D.; Richard L. Ferencz, both of Mount Pleasant; Dietmar Kalz, Summerville, all of S.C.

[73] Assignee: Mobay Chemical Corporation, Pittsburgh, Pa.

[21] Appl. No.: 556,680

[22] Filed: Nov. 30, 1983

[51] Int. Cl.³ .................. C07C 103/127; C07C 102/00
[52] U.S. Cl. ...................................... 564/133; 564/218
[58] Field of Search ................................ 564/218, 133

[56] References Cited

U.S. PATENT DOCUMENTS 4,248,794  2/1981  Fujii et al. ........................... 564/133
4,283,556  8/1981  Lang ............................... 564/133 X

*Primary Examiner*—Paul F. Shaver
*Attorney, Agent, or Firm*—Gene Harsh; Lawrence S. Pope

[57] ABSTRACT

The present disclosure is concerned with a process of reacting a solid aromatic amine with liquid acetic anhydride to yield a solid amide. The amine is in a flowable particulate form and it is subject to sufficient agitation during the reaction to prevent agglomeration. The amide is recovered as a flowable particulate by evaporation of the acetic acid by product and any excess acetic anhydride.

9 Claims, No Drawings

PROCESS FOR THE DIRECT ACETYLATION OF AROMATIC AMINES

FIELD OF THE INVENTION

The present invention is concerned with a procedure for reacting aromatically bound amino groups with acetic anhydride to form acetamide groups.

BACKGROUND OF THE INVENTION

The reaction of primary or secondary amines with carboxylic anhydrides represents a classical preparation of amides. However, in moving from classical chemistry to practical commercial considerations the medium in which the reaction is conducted becomes significantly more important. Means must be provided for bringing the reactants together in a manner which ensures substantially complete reaction, allows for the practical handling of the reactants and the reaction mixture, and provides for the recovery of the desired reaction product in a practically handleable form. Typically this has involved dissolving both the amine and carboxylic anhydride in a process solvent followed by isolation of the amide from the process solvent. Of course it is also possible to simply mix the two reactants in a molten state if they are sufficiently miscible and if there is a set of convenient reaction conditions (temperature and pressure) under which both reactants are in the molten state. However, in such a case the recovery of the finished product may present significant problems particularly if it is solid under these reaction conditions.

An object of the present invention is to provide a procedure whereby aromatic amines may be reacted with acetic anhydride without the use of a process solvent and without the necessity of bringing both reactants to a molten or liquid state. A further object of the present invention is to provide a procedure whereby the product amide may readily be recovered or isolated as free-flowing particles. Another object of the present invention is to provide a procedure whereby the product amide may be isolated by the simple evaporation of acetic acid and acetic anhydride.

SUMMARY OF THE INVENTION

The process of the present invention involves contacting an aromatic amine in particulate form with liquid acetic anhydride under agitation conditions sufficient to prevent the agglomeration of the particles while the amine is converted to the amide. The acetic acid formed by the reaction and any excess acetic anhydride present are then removed by the application of heat and/or vacuum leaving behind the acetylated aromatic amine in particle form. The temperature is controlled during the course of the acetylation reaction and the subsequent evaporation so that neither the aromatic amine starting material nor the aromatic amide product is melted.

DETAILED DESCRIPTION OF THE INVENTION

The process of the present invention may be applied to any aromatic amine which is solid at convenient reaction temperatures and is available as or can be converted to stirrable particles. The process is advantageously applied to monoamines and to amines which have melting points at atmospheric pressure in excess of about 40° C., preferably in excess of about 60° C. A particularly preferred class of aromatic amines are the substituted anilines particularly those which are substituted with either nitro groups or alkoxy groups and those which are substituted with both alkoxy groups and nitro groups. Especially preferred are the ortho, meta and para nitro-substituted anilines and the para-substituted alkoxy especially methoxy-substituted anilines.

The aromatic amines utilized in the process of the present invention should be in the form of stirrable particles, preferably in the form of a free flowing powder. A fine particle size is preferable because of the more favorable surface to volume ratio and consequently faster reaction. Fine powders may be readily utilized. If the amine is not readily available in such a physical form, it may be converted to the appropriate form by cominution techniques known in the art such as room temperature or liquid nitrogen grinding. It is generally preferred that the amine be in this form at room temperature under atmospheric pressure although it is of course possible to practice the present process under elevated pressures or depressed temperatures at which the amine can be obtained as a stirrable particulate.

The reaction should be conducted in an apparatus which has sufficient agitation or shearing capabilities to prevent the permanent agglomeration of the amine particles as they are reacted with the acetic anhydride. Both the acetic anhydride reactant and the acetic acid by-product may act as a solvent for the aromatic amine being acetylated and it may therefore be necessary to continuously disrupt any fusion between partially solvated powder particles which may occur during the course of the reaction.

One suitable type of apparatus is that known to the art for the mixing and applying of shear to pastes and viscous materials. It may be of a continuous or batch-type although for ease of controlling the addition of the acetic anhydride and subsequent evaporation of the unreacted acetic anhydride and by-product acetic acid a batch-type apparatus is preferred. Suitable apparatus is described in pages 4 to 26 of Section 19 of the Fifth Edition of *Chemical Engineers' Handbook*, edited by Perry & Chilton and incorporated herein by reference. Included among these are the heavy duty mixers known to the trade as Baker-Perkins, Warner Pfleiderer, Banbury and Moriyama Feisakusho. Preferred mixers are the double armed dispersion mixers, especially those with mixing blades of the "sigma" type, rotary vacuum dryers with mixing bars, and the plow equipped pressurizable reactors marketed by Littleford Brothers, Inc. The two critical features required of such equipment is the ability to adequately agitate the particles undergoing reaction and the ability to provide an environment whereby the unreacted acetic anhydride and the acetic acid by-product may be readily evaporated away without melting the acetylated amine. This latter condition can be conveniently satisfied by providing equipment in which a vacuum may be applied to the product acetylated amine particles.

Neither the temperature nor the pressure under which the acetylation reaction is conducted are critical so long as they are appropriately selected to maintain the reactants and the reaction product in their proper physical form, i.e. acetic anhydride in liquid form and both the amine and amide in solid form. The reaction is conveniently conducted at temperatures in excess of ambient temperature with reaction temperatures of 60°

C. or higher being particularly preferred. If the reaction is conducted under atmospheric pressure, it is necessary to maintain the reaction temperature below the 140° C. boiling point of acetic anhydride and naturally below the melting point of both the reactant aromatic amine and the product amide. Of course if the reaction is conducted under either pressure or partial vacuum suitable adjustments to the reaction temperature will be necessary.

Appropriate temperature control of the reaction may require reactor cooling, restraints on the acetic anhydride feed rate, or both. The reaction of acetic anhydride with an aromatic amine is exothermic so that control of the reaction temperature will require some means to dissipate this heat of reaction. In a preferred embodiment, the reactor is cooled with chilled water and the feed rate of the acetic anhydride is limited to a rate which maintains the reaction temperature below about 80° C. Naturally, suitable feed rates will depend upon both the particular acetylation reaction being conducted and the thermal transport characteristics of the reactor in which they are conducted. Once the heat of the reaction for a particular amine has been determined, those skilled in the art can readily determine how much heat extraction will be required to maintain the reaction temperature in a desirable range and can then suitably select a reactor with the appropriate thermal transfer characteristics and select an appropriate feed rate.

The acetic anhydride is preferably used in slight molar excess compared to the amino groups to be acetylated with a molar excess of 5% or more being particularly preferred. Any unreacted acetic anhydride can be readily distilled away from the amide product while unreacted amine tends to be somewhat more difficult to separate from the amide. Furthermore, in most cases the acetic anhydride will be the less expensive reactant. In addition, the excess acetic anhydride may act as a drying agent and absorb any water present in the aromatic amine reactant by hydrolyzing to acetic acid. Significant molar excess of as much as 75% of acetic anhydride are not detrimental. Depending on the nature of the agitation apparatus a substantial molar excess may be advantageous in reducing the viscosity of the reaction mixture, thus reducing the load on the agitator.

The aromatic amine being acetylated should be fairly dry. A moisture content of less than 1 wt. % is preferred with a moisture content of less than 0.5 wt. % being particularly preferred. Any moisture present in the amine reactant will tend to consume acetic anhydride. Besides wasting starting material, in those cases in which acetic acid is a solvent for either the amine or the amide this unnecessary generation of acetic acid may make it more difficult to prevent agglomeration of the particles undergoing reaction.

It is preferred that the acetic anhydride utilized be essentially pure. It is expected that any moisture present in the acetic anhydride will readily be hydrolyzed to acetic acid. However, the presence of acetic acid in the acetic anhydride whether from moisture contamination or other sources is undesirable to the extent that it has a solvent effect on either the amine reactant or the amide product because of the likelihood that it will facilitate agglomeration of the particles undergoing reaction. Furthermore, the presence of such an inert liquid is likely to impair the efficiency of the reaction and require extra effort such as longer times, higher temperatures or greater vacuums to isolate the amide product.

The product amide is conveniently isolated by evaporation of both any unreacted acetic anhydride and the by-product acetic acid. This evaporation may be conducted at any convenient pressure so long as the required temperature is below the melting point of the amide product. However, it is preferred to apply at least a partial vacuum after the conversion of the amine to the amide is completed and to raise the temperature until the acetic acid and any acetic anhydride present begin to boil off. Of course, if the reaction temperature was sufficiently high or sufficient vacuum is applied, it may be unnecessary to raise the temperature above that of the reaction temperature. However, it is not preferred to attempt to distill off the acetic acid during the course of the acetylation reaction because of the proximity of the boiling points of acetic acid and acetic anhydride.

The acetylation reaction generally proceeds very rapidly and conversions in excess of 90% have been observed immediately after the addition of a stoichiometric amount of acetic anhydride. In many cases, just the time necessary to raise the reactor temperature to a suitable distillation temperature will be sufficient to complete the conversion. The conversion is normally complete with no amine starting material detectable by HPLC in the product amide. Furthermore, the amide product is generally free of any by-products or impurities not present in the starting material.

The present process has been successfully applied to the acetylation of meta and para nitro aniline utilizing reaction temperatures between about 25° and 70° C. and atmospheric pressure. The product was isolated utilizing a vacuum of approximately 80 mm of Hg and a temperature of approximately 90° C. Utilizing a molar excess of between about 70 and 85% of acetic anhydride product purities between about 95 and 100% were obtained. The process was conducted in a reactor having an agitator that essentially scraped the walls of the reactor and operated at between approximately 200 and 450 rpm.

The present invention is more fully illustrated by the following Examples, which are intended to be non-limiting in nature.

EXAMPLES

EXAMPLE 1

A vertical cylindrical reactor was used that was equipped with an agitator that had a close clearance with the sidewall and bottom of the reactor, (clearances of about 1/16 and 3/16 inches, respectively) and that was designed to prevent any substantial aggolomeration of the contained reactants. The reactor was also equipped with a heating jacket and vapor space thermocouple. The reactor had both an addition port and a vacuum port in its top and was gas tight.

The reactor was loaded with 200.6 g of powdered para-nitro aniline with a moisture content of about 2.9 wt. % (1.41 mols dry material) and a nitrate titration determined purity of 99.4%. The material was dried by heating under vacuum at about 70° C. and the reactor was cooled to about 62° C. Then the agitator was rotated at about 400 rpm while 242.7 g (2.38 mols) of acetic anhydride was added over a period of 75 minutes (about 3 mls/minute). The reactor was then heated to about 86° C. and a vacuum of about 27 inches of Hg was applied. Approximately 197.4 g of distillate was recovered of which 10 to 15 g were estimated to be H$_2$O and the balance acetic acid and acetic anhydride.

The product left in the reactor was a very bright yellow, free flowing powder having a moisture content below about 0.05 wt. %. It has a melting point of 218° C. HPLC analysis indicated the material was essentially pure para-nitro acetanilide.

EXAMPLE 2

The same apparatus was used as in Example 1. The reactor was loaded with 200.6 g of powdered para-nitro aniline with a moisture content of about 2.9 wt. % (1.41 mols dry material) and a nitrite titration determined purity of 99.4%. The material was dried by heating under vacuum to a maximum temperature of about 73° C. The reactor was cooled to about 63° C. Then the agitator was run at about 400 rpm while about 243.6 g (2.39 mol) of acetic anhydride was added over a period of 79 minutes (2.8 mls/minute). The reactor was then heated to about 94° C. and a vacuum was applied. The temperature dropped to about 83° C. and approximately 107.2 g of distillate were obtained.

The product in the reactor was a free flowing yellow powder which was essentially free of moisture and had a melting point of about 217° to 218° C. The reactor also contained a white powder with a similar melting point which turned yellow on melting. The yellow powder was found to be 96.3% para-nitro acetanilide by HPLC.

EXAMPLE 3

The same apparatus was used as in Example 1. The reactor was loaded with 100 g (0.72 mol) of essentially dry powdered meta-nitroaniline with a nitrite titration determined purity of 98%. The reactor was at room temperature (24° C.). While running the agitator at about 425 rpm approximately 123.6 g (1.21 mols) of acetic anhydride was added over the course of 29 minutes (3.9 ml/minute). The agitator experienced an increase in load after the first 10 minutes of addition which was reduced after a further six minutes (total addition of 70 ml of acetic anhydride). The reaction temperature peaked at 31° C. and was 30° C. at the conclusion of the addition. After the addition was completed the reactor was heated to 86° C. and a vacuum was applied. A temperature drop was experienced but the distillation was finished at 86° C.

The product in the reactor was a free flowing caramel colored powder which had a melting point of about 152°–153° C. It was 98.1% meta-nitro-acetanilide by HPLC analysis.

EXAMPLE 4

The same apparatus was used as in Example 1. The reactor was loaded with 2001 g of powdered para-nitroaniline with a moisture content of about 2.8 wt. % (1.41 mol of dry material) and a nitrite titration determined purity of 99.1%. The reactor was heated to 73° C. and a vacuum was applied to dry this material. The reactor was then cooled to room temperature (23° C.). While running the agitator at 225 rpm approximately 267.1 g (2.62 mols) of acetic anhydride was added over about one hour (4.1 ml/minute). During the first 15 minutes the agitator experienced a substantial load which effected its speed of rotation. After the addition was complete the reactor was heated to 79° C. and a vacuum was applied. Approximately 185 g of distillate was collected.

The product in the reactor was a free flowing yellow powder which had a melting point of about 216°–217° C. It was 95.5% para-nitro acetanilide by HPLC analysis.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the acetylation of solid aromatic amines comprising contacting an aromatic amine in flowable particulate form with liquid acetic anhydride under agitation conditions sufficient to prevent the aggolomeration of the particles and then evaporating any unreacted acetic anhydride and the acetic acid by-product without melting the acetylated amine.

2. The process of claim 1 wherein the acetic anhydride and acetic acid are evaporated by the application of heat and vacuum.

3. The process of claim 1 wherein the acetylation reaction is conducted under atmospheric pressure.

4. The process of claim 1 wherein the aromatic amine has a melting point in excess of about 40° C. at atmospheric pressure.

5. The process of claim 4 wherein the amine is an aniline which has a nitro or alkoxy substituent on the aryl ring.

6. The process of claim 1 wherein the amine is a primary amine.

7. The process of claim 1 wherein the aromatic amine is a para or meta nitro aniline.

8. The process of claim 1 wherein the aromatic amine is a methoxy substituted aniline.

9. The process of claim 1 wherein the acetylation reaction is conducted under atmospheric pressure at temperatures between 60° and 70° C., a molar excess of at least about 5% acetic anhydride is utilized, and the acetic acid by-product and unreacted acetic anhydride are removed by the application of partial vacuum and heat.

* * * * *